(12) United States Patent
Ogawa et al.

(10) Patent No.: US 10,653,566 B2
(45) Date of Patent: May 19, 2020

(54) METHOD AND APPARATUS FOR CONTROLLING AND ADVANCING AN ABSORBENT ARTICLE

(71) Applicant: The Procter & Gamble Company, Cincinnati, OH (US)

(72) Inventors: Kazuya Ogawa, Akashi (JP); Matthew Alexander Gittings, Cincinnati, OH (US); Gord E. Graham, Belleville (CA)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/268,535

(22) Filed: Feb. 6, 2019

(65) Prior Publication Data

US 2019/0240077 A1 Aug. 8, 2019

Related U.S. Application Data

(60) Provisional application No. 62/627,228, filed on Feb. 7, 2018.

(51) Int. Cl.
*A61F 13/15* (2006.01)
*B65G 47/244* (2006.01)
*B65G 47/84* (2006.01)

(52) U.S. Cl.
CPC ...... *A61F 13/15764* (2013.01); *B65G 47/244* (2013.01); *B65G 47/848* (2013.01)

(58) Field of Classification Search
CPC ............ A61F 13/15764; B65G 47/244; B65G 47/848
See application file for complete search history.

(56) References Cited

U.S. PATENT DOCUMENTS

| 3,860,003 | A | 1/1975 | Buell |
| 4,695,278 | A | 9/1987 | Lawson |
| 4,704,115 | A | 11/1987 | Buell |
| 4,795,454 | A | 1/1989 | Dragoo |
| 4,909,803 | A | 3/1990 | Aziz et al. |
| 5,091,039 | A * | 2/1992 | Ujimoto ............ A61F 13/15609 |
| | | | 156/519 |
| 6,450,321 | B1 | 9/2002 | Blumenthal et al. |
| 6,705,453 | B2 | 3/2004 | Blumenthal et al. |

(Continued)

OTHER PUBLICATIONS

15124 PCT International Search Report, dated Apr. 24, 2019, 12 pages.

*Primary Examiner* — William R Harp
(74) *Attorney, Agent, or Firm* — C. Brant Cook

(57) ABSTRACT

A converting apparatus operates to control and transfer a folded absorbent article from a first carrier apparatus to a second carrier apparatus. The converting apparatus includes a transfer apparatus and a fluid supply member located adjacent to the transfer apparatus. The transfer apparatus includes a frame that is rotatable about a first axis of rotation and a transfer member that is rotatable about a second axis of rotation. The transfer member defines a receiving surface. The receiving surface includes a plurality of apertures that may operate in cooperation with the fluid supply member to remove any waist region folds in the absorbent article such that a substantially flat absorbent article may be transferred from the transfer apparatus to the second carrier apparatus.

20 Claims, 13 Drawing Sheets

(56) References Cited

U.S. PATENT DOCUMENTS

| | | |
|---|---|---|
| 6,811,019 B2 | 11/2004 | Christian et al. |
| 6,814,217 B2 | 11/2004 | Blumenthal et al. |
| 7,901,393 B2 | 3/2011 | Matsuda et al. |
| 8,607,959 B2 | 12/2013 | Papsdorf et al. |
| 8,720,666 B2 | 5/2014 | Papsdorf et al. |
| 8,820,513 B2 | 9/2014 | Papsdorf et al. |
| 8,833,542 B2 | 9/2014 | Papsdorf et al. |
| 9,150,321 B2 | 10/2015 | Schneider et al. |
| 9,248,053 B2 * | 2/2016 | Ogasawara ....... A61F 13/15699 |
| 9,572,723 B2 | 2/2017 | Schneider et al. |
| 9,764,905 B2 | 9/2017 | Schneider et al. |
| 9,801,763 B2 | 10/2017 | Schneider et al. |
| 2009/0312730 A1 | 12/2009 | LaVon et al. |
| 2013/0211363 A1 | 8/2013 | LaVon et al. |
| 2013/0270065 A1 | 10/2013 | Papsdorf et al. |
| 2014/0112751 A1 | 4/2014 | Schneider et al. |
| 2017/0266059 A1 | 9/2017 | Long et al. |

* cited by examiner

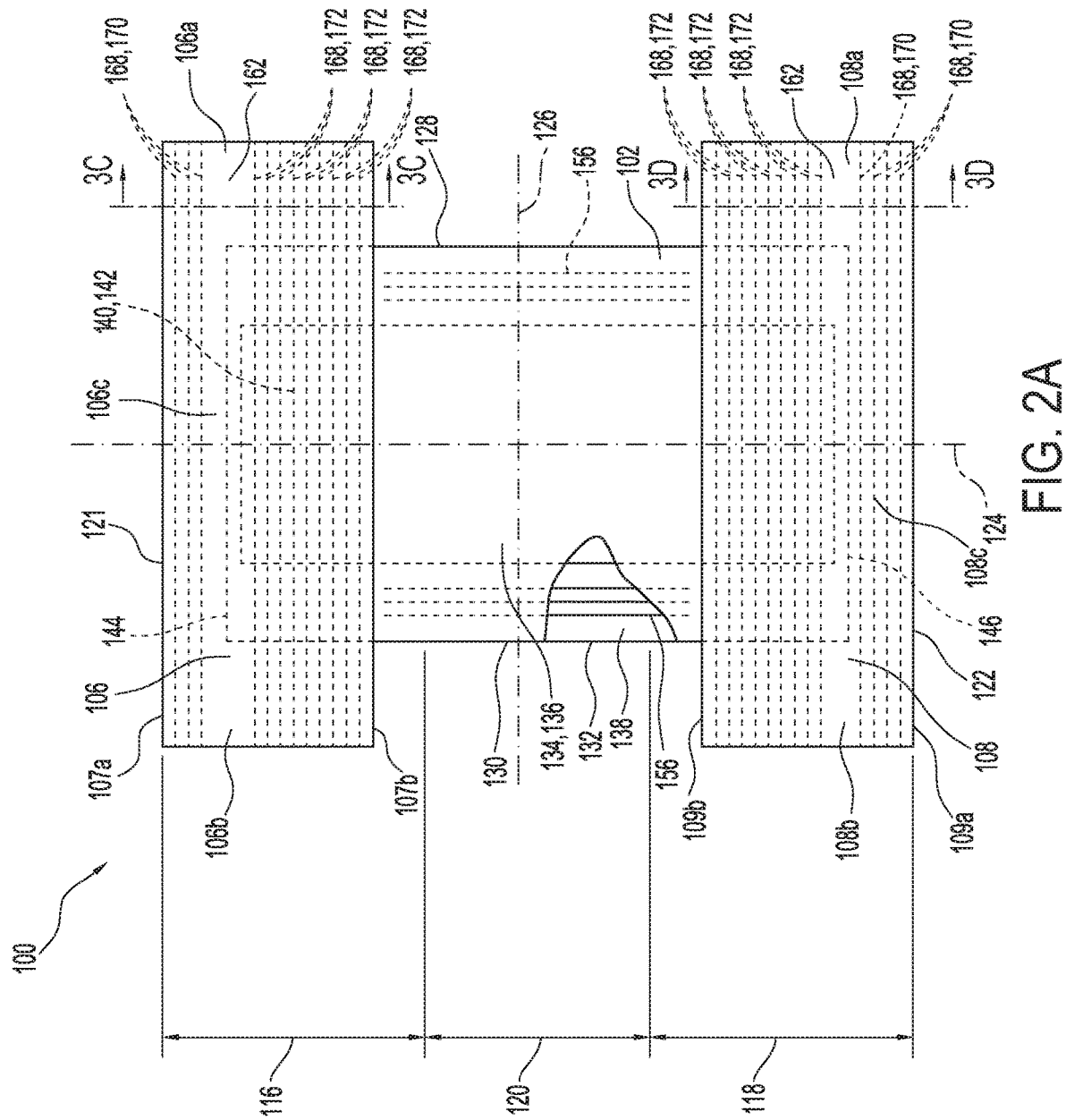

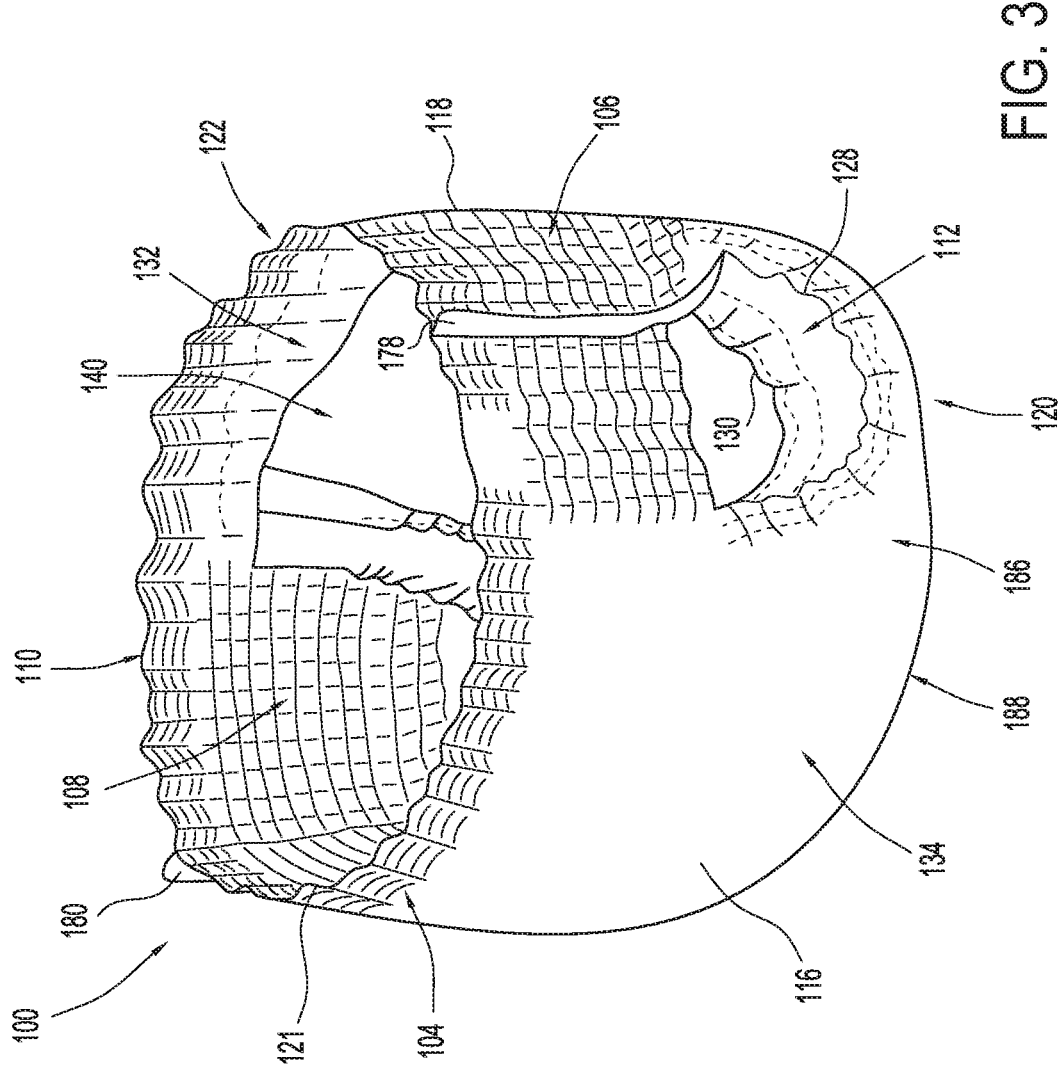

METHOD AND APPARATUS FOR CONTROLLING AND ADVANCING AN ABSORBENT ARTICLE

FIELD

The present disclosure relates to methods and apparatuses for manufacturing absorbent articles, and more particularly, methods and apparatuses for controlling and advancing an absorbent article.

BACKGROUND

Along an assembly line, various types of articles, such as, diapers, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing webs and component parts are subjected to a final knife cut to separate the webs into discrete diapers or other absorbent articles.

It has increasingly become important to save cost on manufacturing processes. To attempt to save costs, the same or similar processes and equipment has been used to produce articles of various sizes. However, the great disparity in size from an adult incontinence pant to a baby pant has caused issues in this attempt to apply the same or similar processes and equipment. For example, the span of the belt of an adult incontinence pant is relatively greater than that of a baby pant. Thus, due to the high speed at which the manufacturing lines operate, control of this relatively large belt has been an issue. Failure to adequately control the belt may lead to final products that have been assembled incorrectly or that have been folded and packaged incorrectly. Failure to control the belt may also lead to manufacturing downtime due to the assembled or partially assembled product become stuck in one or more process. Therefore, it would be beneficial to provide a process and equipment which may be used to manufacture multiple sizes of products and, more specifically, to control and advance relatively larger absorbent articles.

SUMMARY

Aspects of the present disclosure may include a method of transferring discrete absorbent articles from a first carrier apparatus to a second carrier apparatus. In some embodiments, a method of transferring discrete absorbent articles from a first carrier apparatus to a second carrier apparatus includes: advancing an absorbent article with a first carrier apparatus in a machine direction, wherein the absorbent article comprising a belt including a first end region and a second end region separated by a central region, and wherein the first end region comprises a waist region fold; transferring the absorbent article to a transfer apparatus, the transfer apparatus comprising a transfer member connected with a frame, the transfer member including a receiving surface, wherein the receiving surface defines a plurality of apertures, wherein the plurality of apertures is separated into a first group of apertures and a second group of apertures, wherein a fluid supply member is located adjacent to the transfer apparatus; activating at least a portion of the first group of apertures such that the second end region and the central region is held to the receiving surface; rotating the frame about a first axis of rotation; unfolding the waist region fold of the first end region as the frame rotates about the first axis of rotation; applying a positive air pressure from the fluid supply member such that the positive air pressure engages the first end region, wherein the first end region is guided to the receiving surface; activating the second group of apertures such that the first end region is held to the receiving surface; rotating the transfer member about a second axis of rotation as the transfer apparatus rotates about the first axis of rotation, wherein the second axis of rotation is orthogonal to the first axis of rotation; and transferring the absorbent article from the transfer apparatus to a second carrier apparatus.

In some embodiments, a method for advancing an absorbent article may include: advancing an absorbent article in a machine direction wherein the absorbent article comprising a belt including first end region and a second end region separated by a central region; advancing the absorbent article on to a transfer apparatus, wherein the transfer apparatus comprises a frame and a transfer member rotatably connected with the frame, wherein the transfer member includes a receiving surface, wherein the receiving surface comprises a first group of apertures and a second group of apertures; advancing an absorbent article onto the receiving surface of the transfer member, wherein the first group of apertures holds the central portion and the second end region of the absorbent article to the receiving surface; rotating the frame about a first axis of rotation to advance the absorbent article in the machine direction; moving the first end region of the absorbent article with centrifugal force such that the first end region extends away from the receiving surface; applying a positive air pressure from a fluid supply member such that the positive air pressure engages the first end region, wherein the first end region is guided to the receiving surface; and activating the second group of apertures such that the first end region is held to the receiving surface.

In some embodiments, a method of transferring discrete absorbent articles may include: advancing an absorbent article in a machine direction, wherein the absorbent article comprising a belt including first end region and a second end region separated by a central region, and wherein the first end region comprises a waist region fold; transferring the absorbent article to a transfer apparatus, the transfer apparatus comprising a transfer member connected with a frame, the transfer member having a receiving surface, wherein the receiving surface defines a first group of apertures, a second group of apertures, and a third group of apertures positioned between the first group of apertures and the second group of apertures, wherein a fluid supply member is located adjacent to the transfer apparatus; activating the first group of apertures such that the central region and the second end region of the absorbent article is held to the receiving surface; deactivating the third group of apertures; unfolding the waist region fold of the first end region; rotating the frame about a first axis of rotation, wherein the first end region is free to move with respect to the receiving surface; unfolding the waist region fold as the frame rotates about the first axis of rotation; applying a positive air pressure from the fluid supply member such that the positive air pressure engages the first end region, wherein the first end region is guided to the receiving surface; and activating the second group of apertures such that the first end region is held to the receiving surface.

BRIEF DESCRIPTION OF THE DRAWINGS

FIG. 2A is a partially cut-away, plan view of a diaper pant;
FIG. 3 is a schematic, perspective view of a diaper pant.

DETAILED DESCRIPTION

Figure 1:
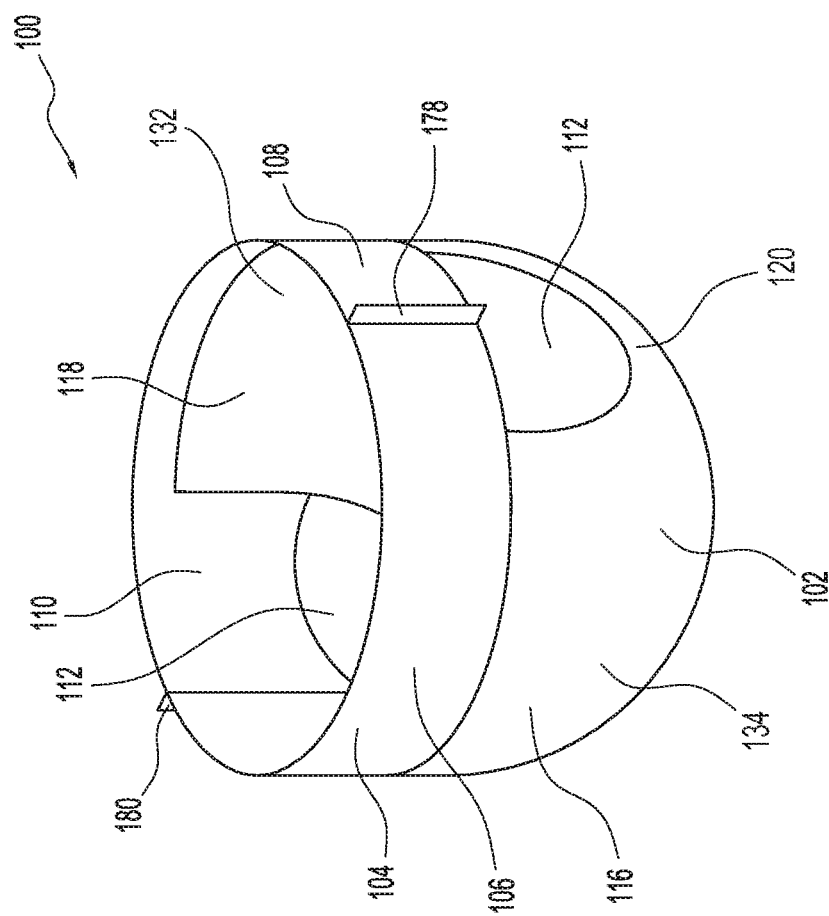
FIG. 1 is a schematic, perspective view of a diaper pant.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Joined" is used herein to encompass configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

"Nonwoven" refers herein to a material made from continuous (long) filaments (fibers) and/or discontinuous (short) filaments (fibers) by processes such as spunbonding, melt-blowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is not parallel with, and is substantially perpendicular to, the machine direction.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

Aspects of the present disclosure involve methods and apparatuses for manufacturing absorbent articles, and more particularly, methods and apparatuses for controlling an advancing absorbent articles. As discussed in more detail below, in a converting process, absorbent articles may be transferred onto a transfer apparatus. The transfer apparatus may be adapted to rotate and reorient the absorbent articles. During the rotating and reorienting process, the absorbent articles may be subjected to centrifugal and/or gravitational forces. The transfer apparatus may include a fluid supply member that is located adjacent to the transfer apparatus and that is configured to control the movement of a portion of the advancing absorbent articles.

The discrete absorbent article may include a chassis having longitudinally opposing first waist and second waist regions separated by a crotch region. The discrete absorbent article may be folded in a U-shape to bring the first waist region into a facing relationship with the second waist region. A ring-like elastic belt may connect the first waist region and the second waist region. The ring-like elastic belt may include a first elastic belt and a second elastic belt. The first and second elastic belts may each be defined by a first end region and a second end region laterally separated by a central region. The first end regions of the first and second elastic belts may be joined to form a first side seam and the second end regions of the first and second elastic belts may be joined to form a second side seam.

A converting apparatus of the present disclosure includes a transfer apparatus for advancing a folded absorbent article from a first carrier apparatus to a second carrier apparatus. The transfer apparatus includes a frame and a plurality of transfer members rotatably connected with the frame. The frame is rotatable about a first axis of rotation and the transfer members are each rotatable about a second axis of rotation. The first axis of rotation extends in a different direction than the second axis of rotation. The first axis of rotation may be orthogonal to the second axis of rotation. The transfer members may define a receiving surface. The converting apparatus also includes a fluid supply member located adjacent to the frame. The fluid supply member may be configured to supply a positive air pressure that engages a portion of the absorbent articles as the absorbent article traverses about the transfer apparatus.

In operation, the folded absorbent article may be transferred from the first carrier apparatus to the transfer apparatus. The folded absorbent article may advance onto the receiving surface of the transfer member. The transfer apparatus advances the folded absorbent article in a machine direction about the first axis of rotation. The transfer member may concurrently rotate the folded absorbent article about the second axis of rotation. The transfer apparatus advances the folded absorbent article past the fluid supply member. The folded absorbent article then advances from the transfer apparatus to the second carrier apparatus.

The fluid supply member operates to control movement of at least a portion of the waist region caused by centrifugal and/or gravitational forces that may act on the advancing folded absorbent article as the absorbent articles advance in the machine direction. It is to be appreciated that controlling the movement of the waist region may assist the absorbent article in advancing to the second carrier apparatus while also controlling the desired orientation of the folded absorbent article for a downstream processing, such as folding and packaging operations.

As previously mentioned, the processes and apparatuses discussed herein may be used to guide an advancing absorbent article. To help provide additional context to the subsequent discussion, the following provides a general description of absorbent articles in the form of diaper pants that may be guided in accordance with the methods and apparatuses disclosed herein. While the present disclosure relates to advancing absorbent articles in the form of diaper pants, it is to be appreciated that the methods and apparatuses disclosed herein may be used with various types of absorbent articles in folded or unfolded configurations. Furthermore, the methods and apparatuses disclosed herein may be used to guide partially assembled diaper components and/or diaper chassis in a variety of converting operations.

FIGS. 1 and 2A illustrate an example of a diaper pant 100 that may be assembled and folded in accordance with the apparatuses and methods disclosed herein. In particular, FIG. 1 illustrates a perspective view of a diaper pant 100 in a pre-fastened configuration and FIG. 2A illustrates a plan view of the diaper pant 100 with the portion of the diaper that faces away from a wearer oriented toward the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region 116, back waist region 118, and crotch region 120 may be one-third of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2A are shown with a longitudinal axis 124 and a lateral axis 126. The longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

Referring to FIG. 2A, the diaper 100 may also include elasticized leg cuffs 156. It is to be appreciated that the leg cuffs 156 can be and are sometimes also referred to as leg bands, side flaps, barrier cuffs, elastic cuffs, or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695, 278; 4,795,454; 4,704,115; 4,909,803; and U.S. patent application Ser. No. 12/434,984.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants 100 may have a continuous perimeter waist opening 110 and continuous perimeter leg openings 112 such as shown in FIG. 1. Various suitable belt layer configurations can be found in U.S. Pat. Appl. Pub. No. 2013/0211363 A1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

Figure 2B:
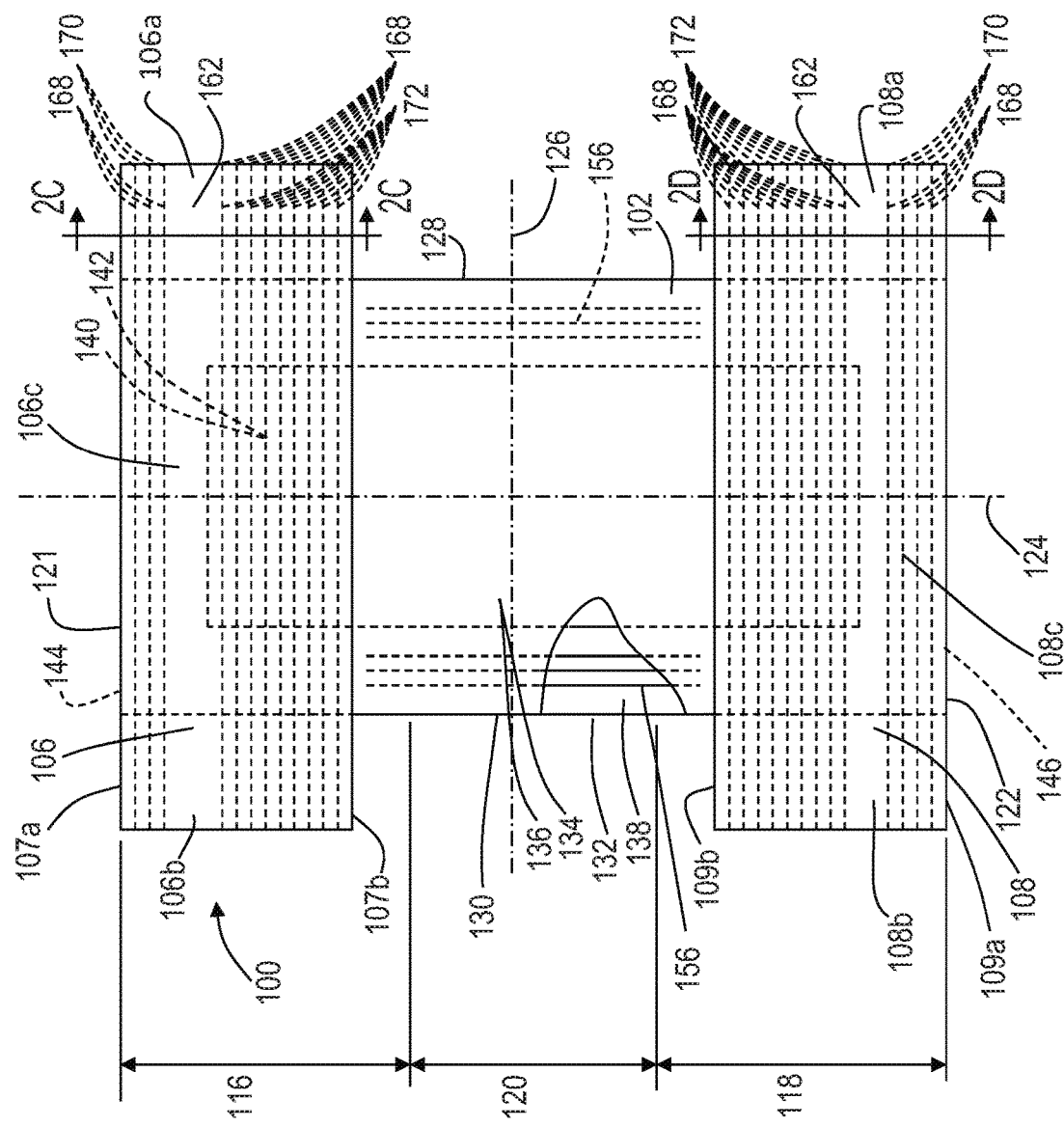
FIG. 2B is a partially cut-away, plan view of a diaper pant.
Figure 2C:
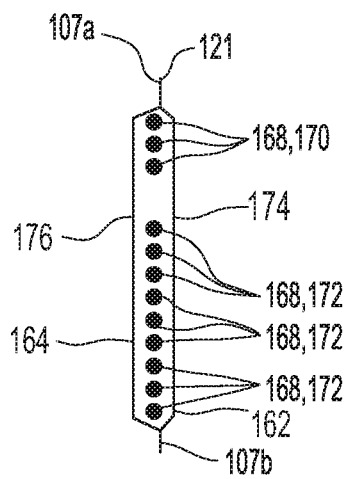
FIG. 2C is a cross-sectional view of the diaper pants of FIGS. 2A and 2B taken along line 2C-2C.
Figure 2D:
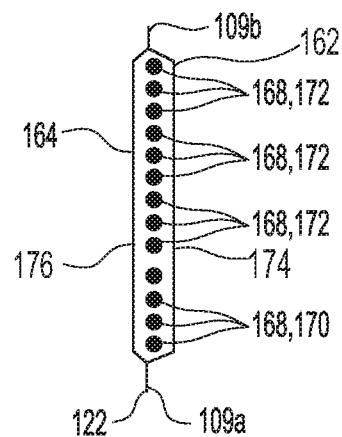
FIG. 2D is a cross-sectional view of the diaper pants of FIGS. 2A and 2B taken along line 2D-2D.

Referring to FIGS. 2A, 2C, and 2D, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt 106 and the second elastic belt 108 may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt 108 may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 2C, and 2D, the belt elastic material may include a plurality of elastic strands 168 which may be referred to herein as outer, waist elastics 170 and inner, waist elastics 172. As shown in FIG. 2, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

It is also to be appreciated that front and back belt end edges and may extend longitudinally beyond the front and back chassis end edges and or they may be co-terminus. The front and back belt side edges may extend laterally beyond the chassis side edges. The front and back belts may be continuous (i.e., having at least one layer that is continuous) from belt side edge to belt side edge. Alternatively, the front and back belts may be discontinuous from belt side edge to belt side edge, such that they are discrete.

As disclosed in U.S. Pat. No. 7,901,393, the longitudinal length (along the longitudinal axis) of the back belt may be greater than the longitudinal length of the front belt, and this may be particularly useful for increased buttocks coverage when the back belt has a greater longitudinal length versus the front belt adjacent to or immediately adjacent to the side seams.

The front outer belt layer and the back outer belt layer may be separated from each other, such that the layers are discrete or, alternatively, these layers may be continuous, such that a layer runs continuously from the front belt end edge to the back belt end edge. This may also be true for the front and back inner belt layers—that is, they may also be longitudinally discrete or continuous. Further, the front and back outer belt layers and may be longitudinally continuous while the front and back inner belt layers are longitudinally discrete, such that a gap is formed between them.

The front and back belts may include slits, holes, and/or perforations providing increased breathability, softness, and a garment-like texture. Underwear-like appearance can be enhanced by substantially aligning the waist and leg edges at the side seams.

In some embodiments, as illustrated in FIG. 3, the diaper pant, which may be referred to herein as an absorbent article, comprises an absorbent main body 188, also referred to herein as chassis 102, to cover the crotch region of the wearer and a belt 104 extending transversely about the waist opening 110. The absorbent article 100 may also comprise an outer cover layer 186 to cover the main body 188. The belt 104 defines the waist opening 110. The belt 104, the main body 188 and/or the outer cover layer 186 jointly define the leg opening 112. One or more of the belt layers may extend from a first waist edge 121 in a first waist region 116 through the crotch region to a longitudinally opposing second waist edge 122 in a second waist region 118 and may form a portion or the whole of the outer surface of the absorbent article 100.

Figure 4A:
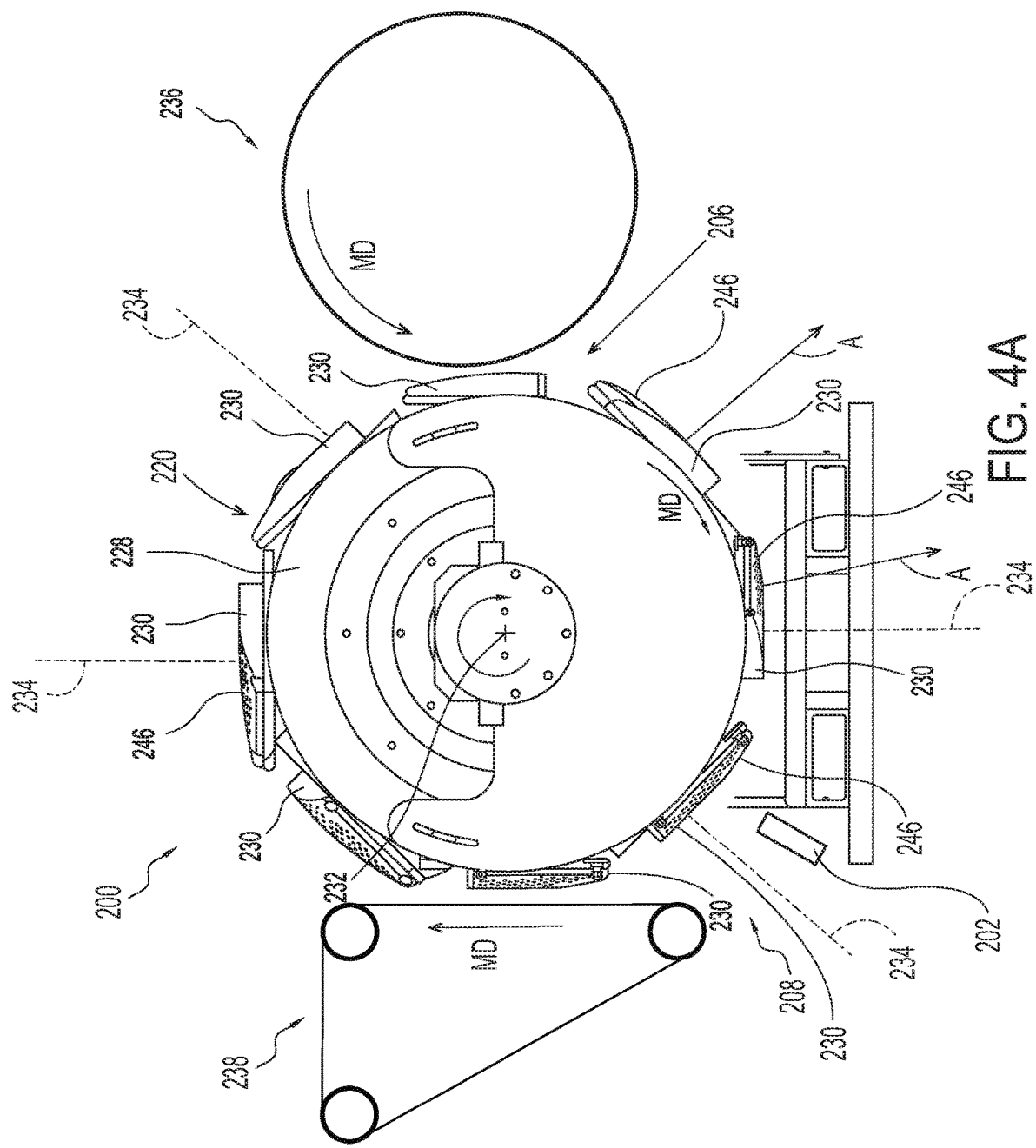
FIG. 4A is a schematic, side elevation view of a transfer apparatus for advancing and controlling a folded diaper pant in a machine direction.
Figure 4B:
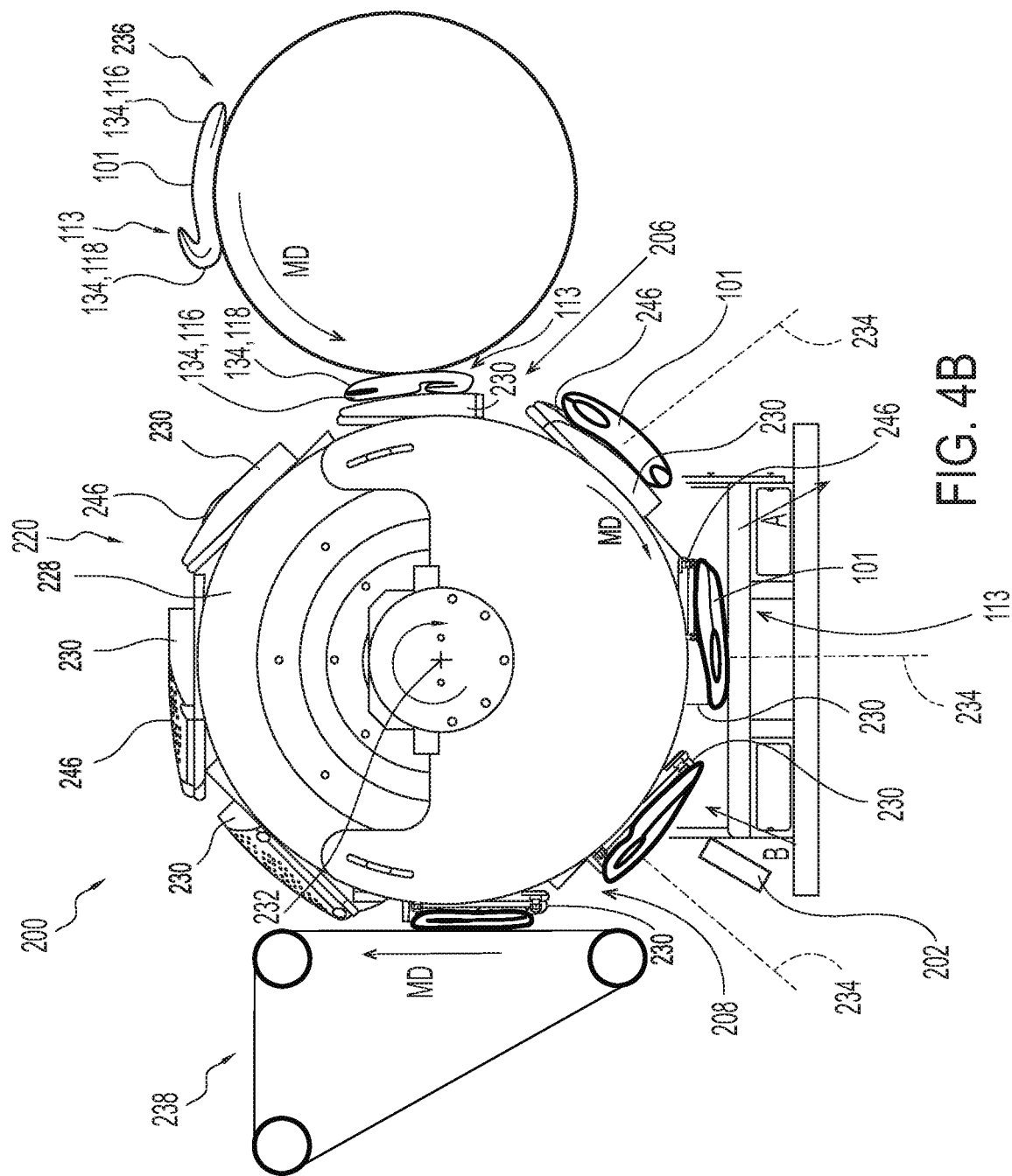
FIG. 4B is a schematic, side elevation view of a transfer apparatus for advancing and controlling a folded diaper pant in a machine direction.

As discussed above, the methods and apparatuses disclosed herein may be used to guide an advancing, folded diaper pant that is subjected to centrifugal and/or gravitational forces. FIGS. 4A and 4B show an exemplary converting apparatus 200 for guiding a folded diaper pant 101. The converting apparatus 200 includes a transfer apparatus 220 having a frame 228 and a plurality of transfer members 230 rotatably connected with the frame 228. The frame 228 may be configured to rotate about a first axis of rotation 232 and the transfer members 230 may be configured to concurrently rotate about a second axis of rotation 234 that extends in a different direction than the first axis of rotation 232. Each transfer member 230 is defined by a receiving surface 246. Exemplary transfer apparatuses are described in U.S. Pat. Nos. 9,150,321 and 9,572,723. The converting apparatus 200 includes a fluid supply member 202 located adjacent to the frame 228 of the transfer apparatus 220. The fluid supply member 202 may be configured to supply positive pressure to at least a portion of the absorbent article. The converting apparatus 200 may include a first carrier apparatus 236 positioned adjacent to a first side portion 206 of the transfer apparatus 220 and a second carrier apparatus 238 positioned adjacent to a second side portion 208 of the transfer apparatus 220. As illustrated in FIGS. 4A and 4B, the first carrier apparatus may include a rotating drum, and the second carrier apparatus may include a conveyor and two or more rollers.

Referring to FIGS. 1, 4A, and 4B, in operation, a folded diaper pant 101 may advance in a machine direction MD onto the first carrier apparatus 236. The outer surface 134 of the second waist region 118 of the folded diaper pant 101 may contact the first carrier apparatus 236 and the outer surface 134 of the first waist region 116 may face away from the first carrier apparatus 236. It is to be appreciated that the folded diaper pants 101 may be subjected to various methods and apparatuses of assembly and construction between being received by the first carrier apparatus 236. Examples of such upstream processes and apparatuses are disclosed in U.S. Pat. Nos. 8,820,513; 8,607,959; 8,833,542; and 8,720,666.

It is to be appreciated that the first and second carrier apparatuses may be configured in various ways. For example, the first and second carrier apparatuses 236, 238 from and to which the diaper pants 101 are transferred may be rolls, drums, curved conveyors, linear conveyors, and/or discrete heads following a curvilinear path, for example. In some embodiments, the first carrier apparatus 236 may be an apparatus such as disclosed in U.S. Pat. Nos. 6,450,321; 6,705,453; 6,811,019; and 6,814,217. In some embodiments, the second carrier apparatus 238 may be an apparatus used to fold the absorbent article, such as disclosed in U.S. Patent Publication Nos. 2017/0266058 A1 and 2017/0266059 A1. The first and second carrier apparatuses 236, 238 may be moving at a different surface velocity or at the same surface velocity as the transfer apparatus 220. For example, the transfer apparatus 220 may pick up the folded diaper pant 101 from the first carrier apparatus 236 at the same velocity as is applied to the folded diaper pant 101 at the second carrier apparatus 238.

As previously discussed, to control manufacturing costs, manufacturing lines are being used to produce products of various sized products. For example, the same or a relatively slightly modified manufacturing line may be used to produce both diaper pants for infants, toddlers, and adults. For relatively larger diaper pants, such as adult, the waist region is relatively large and harder to control in the manufacturing process. For example, in some embodiments, the absorbent article may be transferred from the first carrier apparatus 236 to the transfer apparatus 220 having a fold 113 in the waist region. More specifically, the first carrier apparatus 236 may be unable to control entire length of the waist region of the folded diaper pant 101. Thus, as the first carrier apparatus 236 traverses the folded diaper pant 101 in the machine direction, a portion of the waist region may become folded due to the lack of control by the carrier apparatus 236 and the rotation or movement of the absorbent article by the carrier apparatus 236. A portion of the waist region may fold over itself forming a waist region fold 113, as illustrated in FIG. 4B, as the absorbent article traverses about the first carrier apparatus 236. In some embodiments, the waist region fold 113 may be a fold in a portion of the first and second elastic belts 106, 108. More specifically, the waist region fold 113 may be present in a portion of the elastic belt such as the first end region or the second end region of the elastic belt. The leading portion of the belt, or the portion of the belt that first traverses in the machine direction, is likely to include the waist region fold.

From the first carrier apparatus 236, the outer surface 134 of the first waist region 116 of the folded diaper pant 101 may advance onto a receiving surface 246 of a transfer member 230 as shown in FIG. 4B. The diaper pant 101 may be folded such that, for example, the inner surface 132 of the first waist region 116 is in contact with the inner surface 132 of the second waist region 118, when the diaper pant 101 advances onto the receiving surface 246 of the transfer member 230. The transfer apparatus 220 may rotate the folded diaper pant 101 in the machine direction MD about a first axis of rotation 232.

Further, when the folded diaper pant 101 is transferred from the first carrier apparatus 236 to the transfer member 230, the folded diaper pant 101 may include the waist region fold 113, as illustrated in FIG. 4B. The waist region fold 113 may be such that a portion of the outer surface 134 of the first waist region 116 and a portion of the outer surface of the second waist region 118 are disposed on the receiving surface 246 of the transfer member 230. The waist region fold 113 may be corrected as the folder diaper pant 101 traverses about the first axis of rotation 232 of the frame 228 and the second axis of rotation 234 of the transfer member 230. The waist region fold 113 may be corrected so that additional processes may be performed downstream of the transfer apparatus 220, such as additional folding and packaging of the folded diaper pant. Further, to aid in the transfer of the folded diaper pant 101 to the second carrier apparatus 238, the waist region fold 113 may be removed such that a substantially flat folded diaper pant 101 is transferred to the second carrier apparatus 238.

As previously discussed, the transfer apparatus 229 may include a transfer member 230 including a receiving surface 246. The receiving surface 246 may define a plurality of apertures 260. The plurality of apertures 260 may be operatively connected to a vacuum source such that fluid is pulled through the apertures toward the first axis of rotation 232 of the frame 228. The plurality of apertures 260 may also be operatively connected to a fluid source such that pressurized fluid is expelled through the apertures in a direction away from the first axis of rotation 232 of the frame 228. Each of the apertures of the plurality of apertures may be individually controlled or the apertures may be grouped such that different groups of apertures are in operation at different times and/or different groups of apertures perform different functions, such as supplying a positive fluid pressure or creating a vacuum. Having the plurality of apertures supply a positive fluid pressure may aid in removing the folded diaper pant 101 from the receiving surface 246. Having the plurality of apertures supply a vacuum may aid in transferring the folded diaper pant onto the receiving surface 246 and maintaining the folded diaper pant against the receiving surface 246 as the transfer members 230 traverse about the first axis of rotation 232.

Figure 5A:
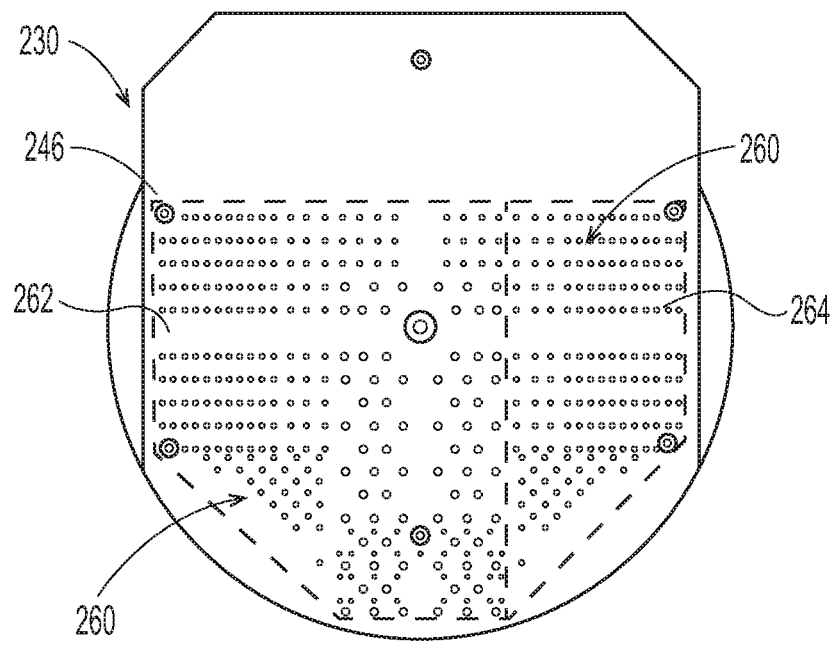
FIG. 5A is a schematic, top view of a transfer member including a receiving surface.

The plurality of apertures 260 may be arranged in any configuration that allows the folder diaper pant 101 to be transferred to, to be held in place by, and to be removed from the transfer member 230. For example, as illustrated in FIG. 5A, the plurality of apertures 260 may be arranged on the receiving surface 246 in a pattern generally the same as the folded diaper pant 101.

As previously discussed, the plurality of apertures may be grouped such that groups of apertures are controlled individually. For example, in some embodiments, the plurality of apertures 260 may be grouped into a first group of apertures 262 and a second group of apertures 264, as illustrated in FIG. 5A. The first group of apertures 262 may be controlled independent of the second group of apertures 264. For example, the folded diaper pant may be received by the receiving surface 246. The first group of apertures 262 may be activated such that vacuum is provided by the first group of apertures 262. This first group of apertures 262 holds a first portion of the folded diaper pant 101 on the receive surface 246. The first portion of the folded diaper pant 101 may include the central portion and the first end region of the belt, as illustrated in FIG. 2B. However, the second group of apertures 264 may remain deactivated as the folded diaper pant 101 is transferred to the receiving surface 246. This may be the portion of the folded diaper pant 101 that includes the waist region fold 113, which may be present in the second end region of the belt. This allows the waist region fold 113 to move with respect to the receiving surface 246 as the transfer member 230 traverses about the first axis of rotation 232.

As previously discussed, having a waist region fold 113 in the folded diaper pant 101 would be undesirable for transfer to the second carrier apparatus and for downstream processing, such as folding and packaging. Thus, to remove the waist region fold 113, the portion of the folded diaper pant 101 including the waist region fold 113, which may be the second end region of the belt, is not held to the receiving surface 246 and, rather, is allowed to move with respect to the receiving surface 246. More specifically, as the frame 228 rotates about the first axis of rotation 232 and the transfer member 230, including the receiving surface 246, rotates about the second axis of rotation 234, the second end region, including the waist region fold 113, is subject to centrifugal and/or gravitational forces such that the second end region extends away from the receiving surface 246, which results in the waist region fold 113 being unfolded, as illustrated in FIG. 4B.

The folded diaper pant 101 continues to traverse about the first axis of rotation 232. As the folded diaper pant 101 traverses about the first axis of rotation 232 and the second end region of the folded diaper pant extends away from the receiving surface and unfolds, the folded diaper pant traverses past a fluid supply member 202. The fluid supply member 202 is positioned adjacent to the frame 228 and the receiving surface 246 such that the fluid supply member 202 may provide a positive air pressure. The positive air pressure expelled from the fluid supply member 202 may engage the second end region or the region of the belt that has extended away from the receiving surface 246. This engagement of the positive air pressure causes the extended belt region to be guided back toward the receiving surface 246. Further, the second group of apertures 264 may be activated to aid in guiding the belt region back toward the receiving surface 246 and, subsequently, holding the belt region to the receiving surface 246 as the folded diaper pant 101 continues to traverse in the machine direction MD. The folded diaper pant 101 lays substantially flat against the receiving surface 246 as the folded diaper pant 101 continues to traverse in the machine direction toward the second carrier apparatus 238.

The positive air pressure may be expelled at greater than or equal to about 0.5 bar. In some embodiments, the fluid supply member may expel a positive air pressure at from about 0.5 bar to about 8 bar and/or from about 1 bar to about 6 bar, including all 0.1 bar increments within the specified ranges and all ranges formed therein or thereby.

The substantially flat, folded diaper pant 101 may then be transferred to the second carrier apparatus 238. The first and second groups of apertures 262, 264 may be used to aid the transfer of the folded diaper pant 101 to the second carrier apparatus 238. The first and second groups of apertures 262, 264 may expel pressurized fluid to aid in the removal of the folded diaper pant from the receiving surface 246 of the transfer member 230 to the second carrier apparatus 238. The folded diaper pant 101 may be transferred in a substantially flat configuration to aid in downstream processes, such as additional folding and packaging. It is to be appreciated that certain apertures may be used only to supply vacuum or to supply pressurized fluid. Each of the apertures may be independently controlled for optimal handling of the diaper pant 101.

Figure 5B:
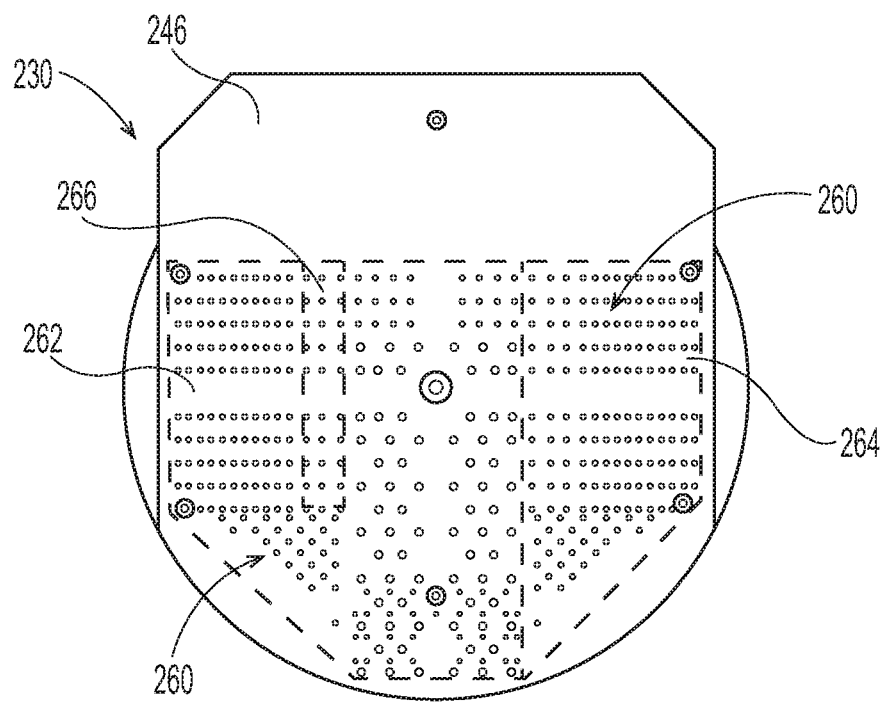
FIG. 5B is a schematic, top view of a transfer member including a receiving surface.

It is to be appreciated that the plurality of apertures 260 may be divided into any number of groups to aid in receiving, holding, and transferring the folded diaper pant. For example, the plurality of apertures 260 may be divided into a first group of apertures 262, a second group of apertures 264, and a third group of apertures 266, as illustrated in FIG. 5B. These three groups of apertures may aid in allowing the second end region to unfold as the folded diaper pant traverses about the first axis of rotation. More specifically, for example, the folded diaper pant 101 including the waist region fold 113 may be transferred onto the receiving surface 246 of the transfer member 230. The central region and the first end region may be disposed on the first group of apertures 262. The second end region may be disposed on the second group of apertures 264, and a portion of the central region and/or the first end region may also be disposed on the third group of apertures 266. The groups of apertures may be controlled to aid in receiving the folded diaper pant 101 and removing the waist region fold 113.

For example, when the folded diaper pant 101 including the waist region fold 113 is transferred to the receiving surface, the first group of apertures may be activated such that fluid is pulled through the apertures toward the first axis of rotation creating vacuum. The vacuum pulls the first end region and the central region to the receiving surface. The second group of apertures and the third group of apertures may remain deactivated. The second end region, including the waist region fold 113, may be disposed on the second group of apertures. The third group of apertures remains deactivated during the transfer of the folded diaper pant 101 onto the receiving surface 246 and as the transfer member traverses 230 about the first axis of rotation 234. Having this third group of apertures remain deactivated aids in the unfolding of the waist region fold 113. More specifically, the second end region including the waist region fold 113 is free to move with respect to the receiving surface 246, due to the inactivation of the second group of apertures. However, as the second end region becomes affected by the centrifugal and/or gravitational forces as the transfer member 230 traverses, the second end region may fold such that at least a portion of the second end region folds over the central region and into the first end region of the folded diaper pant. By having the third group of apertures be deactivated, the second end region that folds over into the first end region is not held by the vacuum supplied by the apertures. Stated another way, the third group of apertures may remain deactivated during the transfer and partial traversal of the folded diaper pant, such that the second end region remains free to move with respect to the receiving surface and does not become restricted by the vacuum provided by the apertures.

It is to be appreciated that either or both of the first and second groups of apertures may be activated once the fluid supply member 202 acts on the second end region and, thus, substantially flattens the second end region to the receiving surface 246. It is also to be appreciated that the third group of apertures may be activated such that vacuum is supplied once the second end region is substantially flattened to the receiving surface 246. Alternatively, the third group of apertures may remain deactivated while the folded diaper pant traverses about the first axis of rotation from the first carrier apparatus to the second carrier apparatus. When the transfer member 230 carrying the substantially flat, folded diaper pant 101 reaches the second carrier apparatus 238 at least one of the first group of apertures, the second group of apertures, and the third group of apertures may be activated to supply a positive fluid pressure, such that fluid is expelled through the apertures in a direction away from the first axis of rotation. This positive fluid pressure may aid in removing the folded diaper pant from the transfer member.

It is to be appreciated that the plurality of apertures may be controlled in any number of groups to better control the folded diaper pant and to put the folded diaper pant in a state, such as a substantially flat orientation, desirable for downstream processing, such as folding and packaging.

Figure 6A:
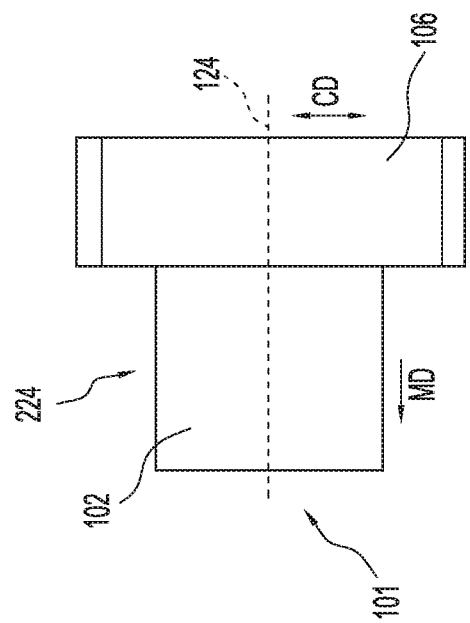
FIG. 6A is a schematic, plan view of a folded diaper pant in a first orientation.
Figure 6B:
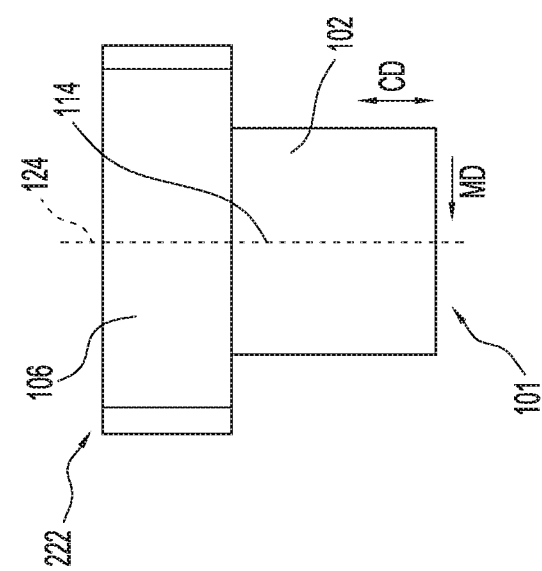
FIG. 6B is a schematic, plan view of a folded diaper pant in a second orientation.

Referring to FIG. 4B, the folded diaper pant 101 may transfer from the first carrier apparatus 236 to the transfer apparatus 220 in a first orientation. As shown in FIG. 6A, in the first orientation 222, the longitudinal axis 124 of the folded diaper pant 101 extends in the cross direction CD. The transfer apparatus 220 advances the folded diaper pant 101 in the machine direction MD about the first axis of rotation 232 while the transfer member 230 rotates the folded diaper pant 101 about the second axis of rotation 234. As shown in FIG. 4B, centrifugal and/or gravitational forces pull the second end region of the folded diaper pant 101 in the first direction, A, away from the first axis of rotation 232. As the frame 228 continues rotating about the first axis of rotation 232, the second end region is engaged by the fluid supply member 202, which supplies pressurized fluid to control the second end region, and causing the second end region to move toward the receiving surface in a second direction, B, toward the first axis of rotation 232. The folded diaper pant 101 may lay substantially flat against the receiving surface 246 before advancing onto the second carrier apparatus 238. The folded diaper pant 101 is in a second orientation as the folded diaper pant 101 advances onto the second carrier apparatus 238. In the second orientation 224, the longitudinal axis 124 of the folded diaper pant 101 extends in the machine direction MD as shown in FIG. 6B. It is to be appreciated that the transfer member 230 may rotate the folded diaper pant 101 any number of degrees about the second axis of rotation. For example, the transfer member may rotate the folded diaper pant 101 90 degrees about the second axis of rotation.

Figure 7:
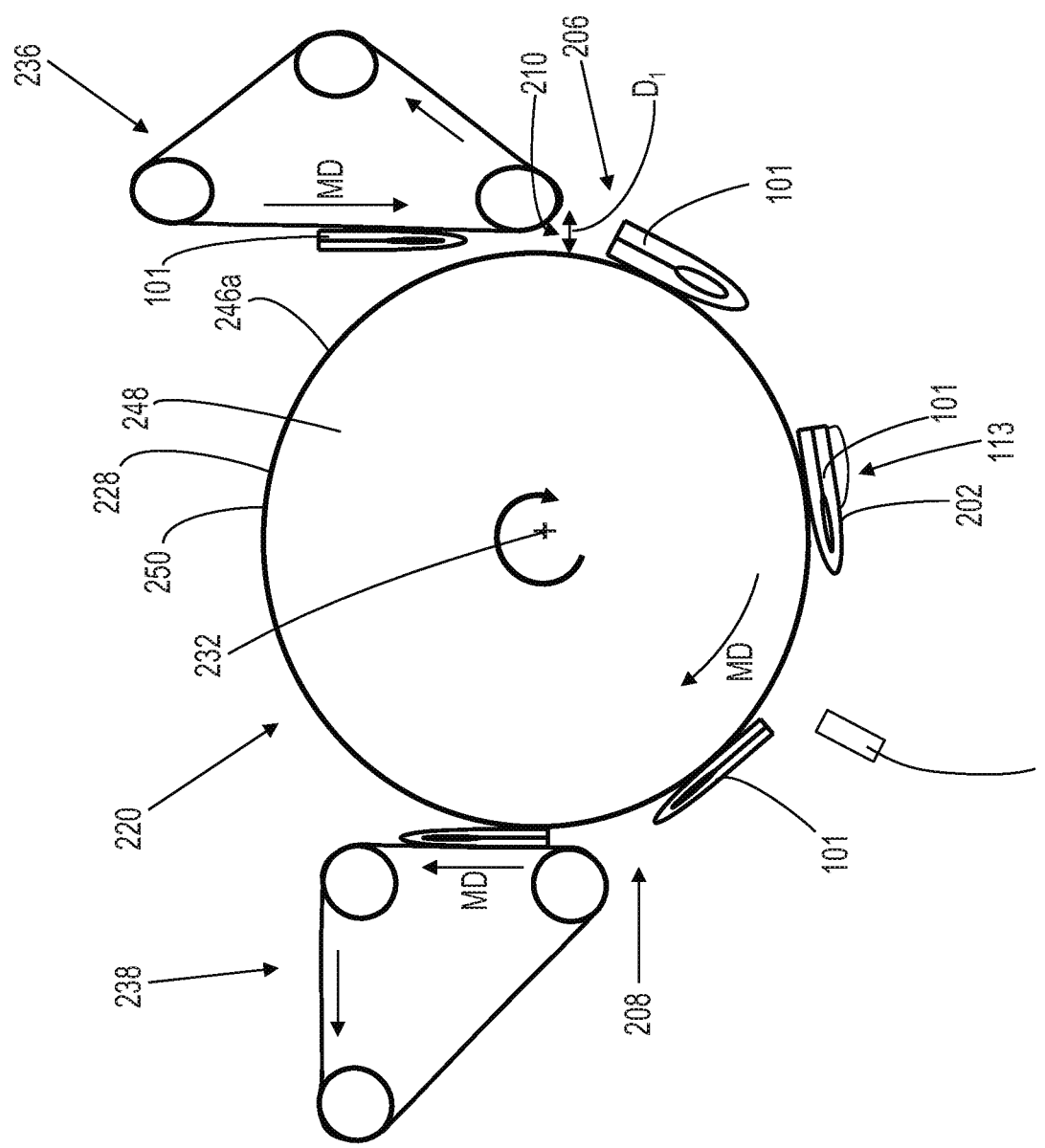
FIG. 7 is a schematic, side elevation view of a transfer apparatus having a frame in the form of a drum.

The frame 228 of the transfer apparatus 220 may be configured in various different ways. For example, as shown in FIG. 7, the frame 228 may be configured as a drum 248. The drum 248 may include an outer circumferential surface 250 that forms a receiving surface 246a for advancing the folded diaper pants 101. It is to be appreciated that the frame 228 may be configured in various other way for advancing the folded diaper pant in the machine direction MD; for example, the frame may comprise a conveyor or a series of rollers.

Figure 8:
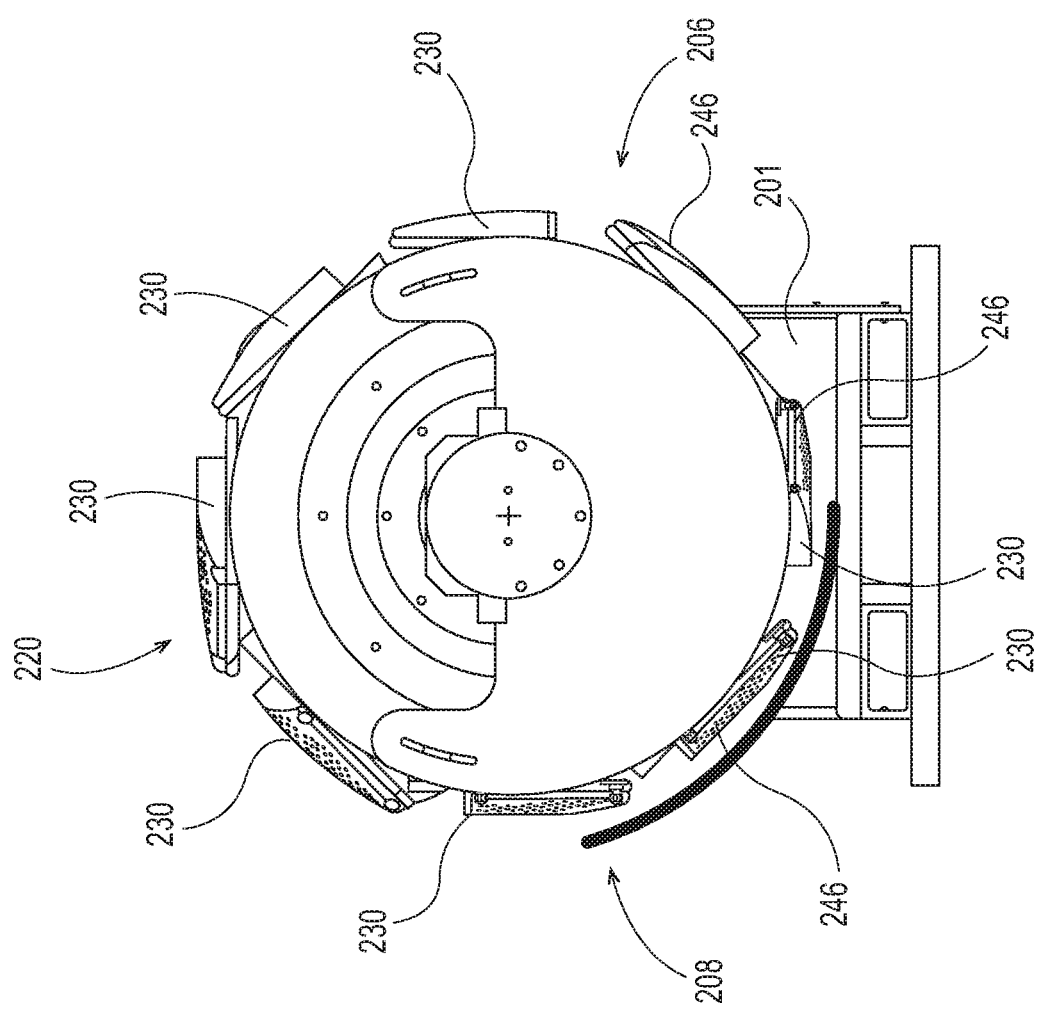
FIG. 8 is a schematic, side elevation view of a transfer apparatus including a guide member.
Figure 9:
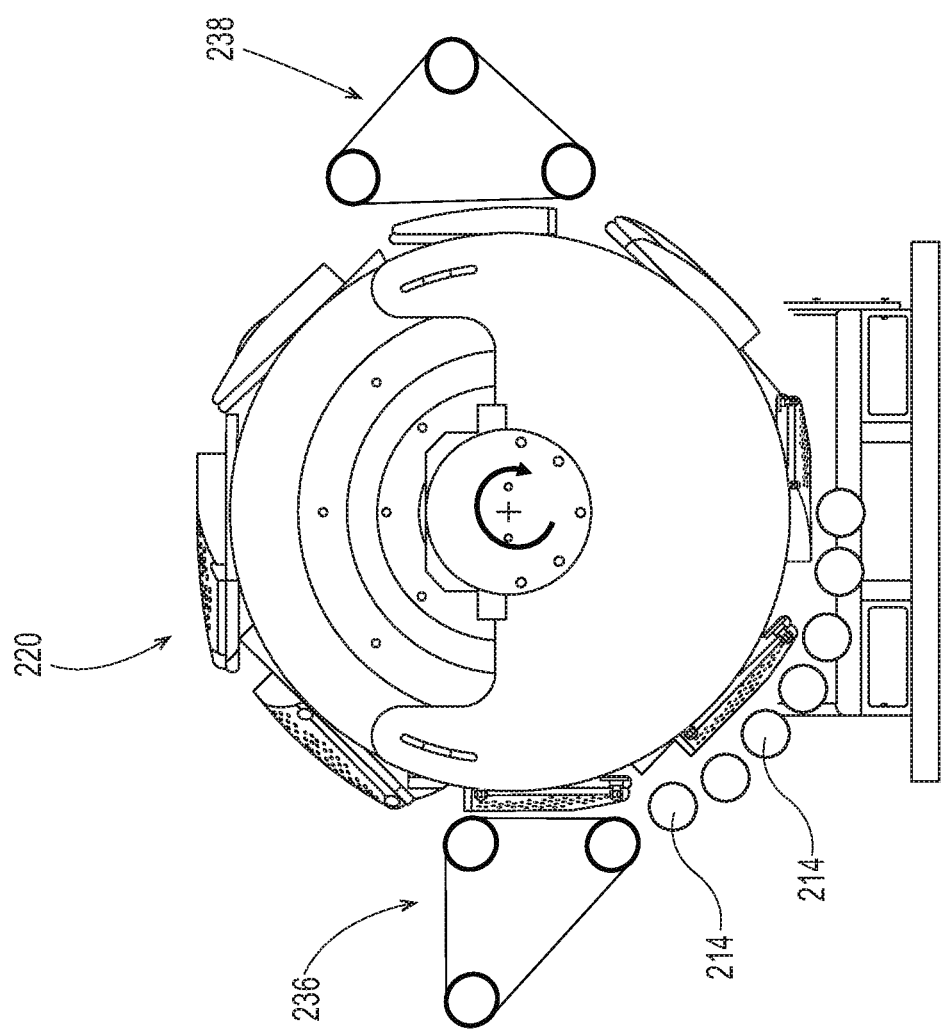
FIG. 9 is a schematic, side elevation view of a transfer apparatus including a plurality of rollers.
Figure 10:
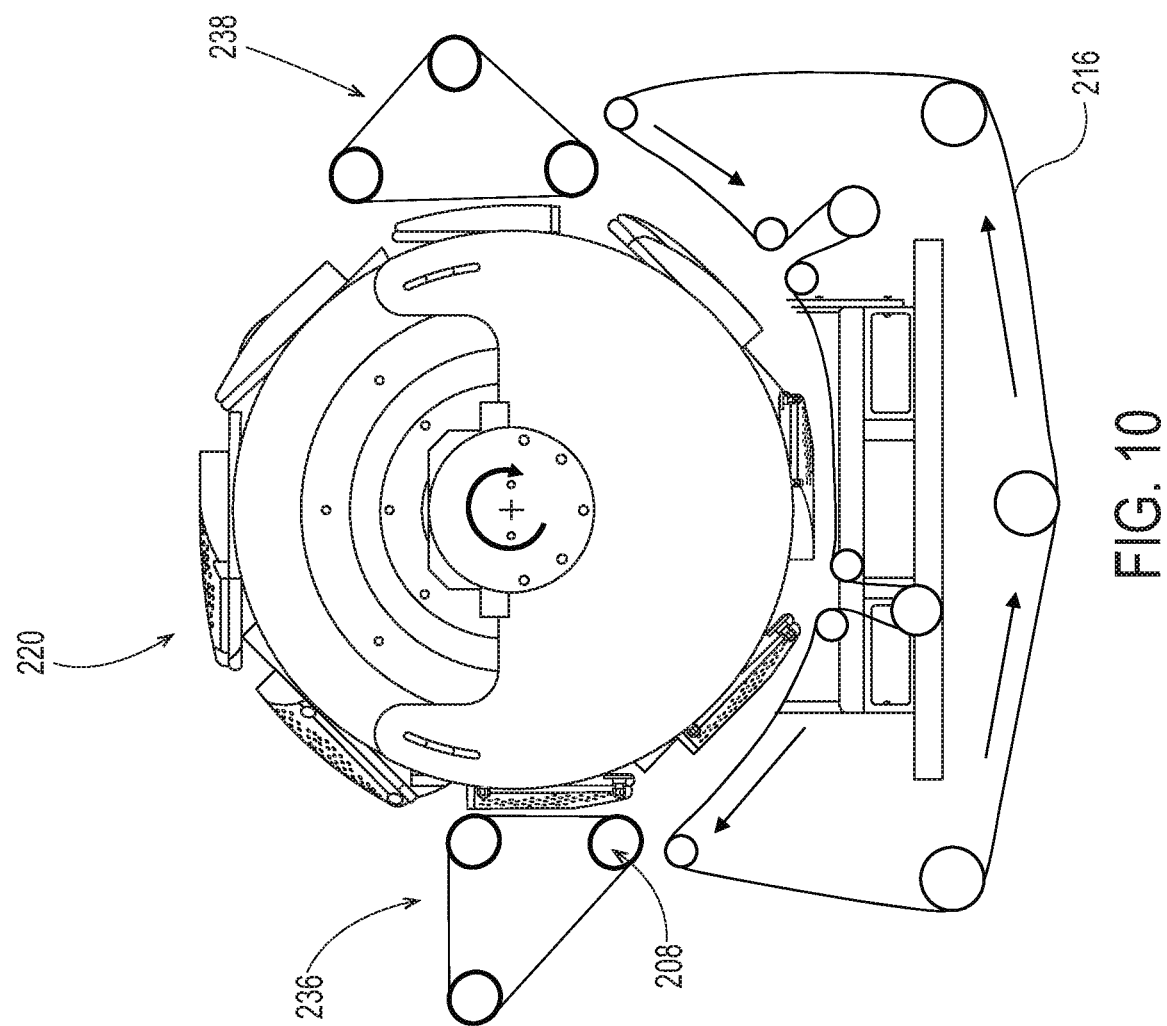
FIG. 10 is a schematic, side elevation view of a transfer apparatus including a conveyor.

In another exemplary configuration, shown in FIG. 8, a guide member 201 may be used to control the second end region and to place the folded diaper pant in a substantially flat configuration. The guide member 201 may include a plurality of apertures through which fluid may be expelled to aid in controlling the belt. The plurality of apertures may be arranged and function such as disclosed in U.S. Pat. Nos. 9,764,905 and 9,801,763. In another exemplary configuration, such as illustrated in FIG. 9, a series of rollers 214 may be used to control the second end region and to place the folded diaper pant in a substantially flat configuration. In other exemplary configurations, such as shown in FIG. 10, a conveyor 216 may be used. It is to be appreciated that in a configuration such as a guide member 201, a series of rollers 214, or as a conveyor 216, the surface may be moveable in order to guide the folded diaper pants in the machine direction MD. The surface may be configured such that the coefficient of friction between the surface and the folded diaper pant is relatively low. The guide member 201, rollers 214 and the conveyor 216 may be configured to apply a positive pressure to the folded diaper pant advancing about the first axis of rotation 232.

This application claims the benefit of U.S. Provisional Application No. 62/627,228 filed on Feb. 7, 2018, which is incorporated herein by reference.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of transferring discrete absorbent articles from a first carrier apparatus to a second carrier apparatus, the method comprising:
   advancing an absorbent article with a first carrier apparatus in a machine direction, wherein the absorbent article comprising a belt including a first end region and a second end region separated by a central region, and wherein the first end region comprises a waist region fold;
   transferring the absorbent article to a transfer apparatus, the transfer apparatus comprising a transfer member connected with a frame, the transfer member including a receiving surface, wherein the receiving surface defines a plurality of apertures, wherein the plurality of apertures is separated into a first group of apertures and a second group of apertures, wherein a fluid supply member is located adjacent to the transfer apparatus;
   activating at least a portion of the first group of apertures by fluid being pulled through the apertures creating vacuum such that the second end region and the central region are held to the receiving surface;
   rotating the frame about a first axis of rotation;
   unfolding the waist region fold of the first end region as the frame rotates about the first axis of rotation;
   applying a positive air pressure from the fluid supply member such that the positive air pressure engages the first end region, wherein the first end region is guided to the receiving surface;
   activating the second group of apertures by fluid being pulled through the apertures creating vacuum such that the first end region is held to the receiving surface;
   rotating the transfer member about a second axis of rotation as the transfer apparatus rotates about the first axis of rotation, wherein the second axis of rotation is orthogonal to the first axis of rotation; and
   transferring the absorbent article from the transfer apparatus to a second carrier apparatus.

2. The method of claim 1, wherein the first end region folds over at least a portion of at least one of the central region and the second end region as the transfer apparatus rotates about the first axis of rotation.

3. The method of claim 1, wherein the first group of apertures comprises a first portion and a second portion.

4. The method of claim 3, wherein the first portion of the first group of apertures supply vacuum and the second portion of the first group of apertures does not supply vacuum.

5. The method of claim 3, wherein the first portion of the first group of apertures supply vacuum and the second portion of the first group of apertures supply vacuum.

6. The method of claim 1, wherein the positive air pressure is provided at greater than about 0.5 bar.

7. The method of claim 1, wherein the positive air pressure is provided at a pressure from about 0.5 bar to about 8 bar.

8. A method for advancing an absorbent article, the method comprising:
   advancing an absorbent article in a machine direction wherein the absorbent article comprising a belt including first end region and a second end region separated by a central region;
   advancing the absorbent article on to a transfer apparatus, wherein the transfer apparatus comprises a frame and a transfer member rotatably connected with the frame, wherein the transfer member includes a receiving surface, wherein the receiving surface comprises a first group of apertures and a second group of apertures;
   advancing an absorbent article onto the receiving surface of the transfer member, wherein the first group of apertures holds the central portion and the second end region of the absorbent article to the receiving surface;
   rotating the frame about a first axis of rotation to advance the absorbent article in the machine direction;
   moving the first end region of the absorbent article with centrifugal force such that the first end region extends away from the receiving surface;
   applying a positive air pressure from a fluid supply member such that the positive air pressure engages the first end region, wherein the first end region is guided to the receiving surface; and
   activating the second group of apertures by fluid being pulled through the apertures creating vacuum such that the first end region is held to the receiving surface.

9. The method of claim 8, wherein the absorbent article comprises a first waist region and a second waist region separated by a crotch region, wherein the first waist region comprises a first elastic belt and the second waist region comprises a second elastic belt, wherein the first elastic belt is joined with the second elastic belt to form first and second side seams.

10. The method of claim 9, wherein the first waist region of the absorbent article contacts the receiving surface as the absorbent article advances on the transfer member and the second waist region is adjacent to the fluid supply member as the absorbent article is advanced.

11. The method of claim 8, wherein the positive air pressure is supplied by the fluid supply member at a pressure from about 0.5 bar to about 8 bars.

12. The method of claim 8, further comprising concurrently rotating the transfer member about a second axis of rotation as the frame rotates about the first axis of rotation, wherein the second axis of rotation is orthogonal to the first axis of rotation.

13. The method of claim 8, further comprising transferring the absorbent article from the transfer apparatus to a second carrier apparatus.

14. The method of claim 8, wherein the first end region is free to move relative to the receiving surface as the frame rotates about the first axis of rotation.

15. The method of claim 8, wherein a portion of the first group of apertures does not supply vacuum.

16. A method of transferring discrete absorbent articles, the method comprising:

advancing an absorbent article in a machine direction, wherein the absorbent article comprising a belt including first end region and a second end region separated by a central region, and wherein the first end region comprises a waist region fold;

transferring the absorbent article to a transfer apparatus, the transfer apparatus comprising a transfer member connected with a frame, the transfer member having a receiving surface, wherein the receiving surface defines a first group of apertures, a second group of apertures, and a third group of apertures positioned between the first group of apertures and the second group of apertures, wherein a fluid supply member is located adjacent to the transfer apparatus;

activating the first group of apertures by fluid being pulled through the aperture creating vacuum such that the central region and the second end region of the absorbent article are held to the receiving surface;

deactivating the third group of apertures to not supply vacuum;

unfolding the waist region fold of the first end region;

rotating the frame about a first axis of rotation, wherein the first end region is free to move with respect to the receiving surface;

unfolding the waist region fold as the frame rotates about the first axis of rotation;

applying a positive air pressure from the fluid supply member such that the positive air pressure engages the first end region, wherein the first end region is guided to the receiving surface; and activating the second group of apertures by fluid being pulled through the aperture creating vacuum such that the first end region is held to the receiving surface.

17. The method of claim 16, comprising transferring the absorbent article from a first carrier apparatus to the transfer apparatus.

18. The method of claim 17, wherein the absorbent article is a diaper pant.

19. The method of claim 16, comprising rotating the transfer member about a second axis of rotation as the transfer apparatus rotates about the first axis of rotation, wherein the second axis of rotation is orthogonal to the first axis of rotation.

20. The method of claim 16, comprising supplying a positive pressure through at least one of the first group of apertures, the second group of apertures, and the third group of apertures to transfer the absorbent article from the transfer apparatus to the second carrier apparatus.

* * * * *